(12) United States Patent
Huang

(10) Patent No.: US 8,040,510 B2
(45) Date of Patent: Oct. 18, 2011

(54) SPATIALLY PRECISE OPTICAL TREATMENT OR MEASUREMENT OF TARGETS THROUGH INTERVENING BIREFRINGENT LAYERS

(75) Inventor: Fang Huang, Fremont, CA (US)

(73) Assignee: NovaSolar Holdings Limited, Tortola (VG)

( * ) Notice: Subject to any disclaimer, the term of this patent is extended or adjusted under 35 U.S.C. 154(b) by 289 days.

(21) Appl. No.: 12/196,455

(22) Filed: Aug. 22, 2008

(65) Prior Publication Data

US 2010/0045983 A1    Feb. 25, 2010

(51) Int. Cl.
*G01J 4/00* (2006.01)
(52) U.S. Cl. .................. 356/365; 356/364; 356/367
(58) Field of Classification Search .......... 356/364–370, 356/445; 250/225, 201.1, 559.4; 359/497, 359/494, 499
See application file for complete search history.

(56) References Cited

U.S. PATENT DOCUMENTS

| | | | | |
|---|---|---|---|---|
| 3,724,938 A | * | 4/1973 | Nepela | 353/20 |
| 5,650,938 A | * | 7/1997 | Bootehsaz et al. | 716/102 |
| 5,694,384 A | * | 12/1997 | Luster | 369/110.01 |
| 6,031,614 A | * | 2/2000 | Michaelis et al. | 356/369 |
| 6,055,053 A | * | 4/2000 | Lesniak | 356/366 |
| 6,943,869 B2 | * | 9/2005 | Hubner et al. | 356/34 |
| 6,982,792 B1 | * | 1/2006 | Woollam et al. | 356/369 |
| 7,046,363 B2 | * | 5/2006 | Michaelis et al. | 356/445 |
| 7,099,081 B2 | * | 8/2006 | Norton et al. | 359/497 |
| 7,298,471 B2 | * | 11/2007 | Fukazawa et al. | 356/237.5 |
| 7,347,556 B2 | * | 3/2008 | Kasik et al. | 353/8 |
| 2008/0049321 A1 | * | 2/2008 | McEldowney et al. | 359/494 |

* cited by examiner

*Primary Examiner* — Sang Nguyen
(74) *Attorney, Agent, or Firm* — Schwabe, Williamson & Wyatt, P.C.

(57) ABSTRACT

A treatment pattern (such as a focused spot, an image, or an interferogram) projected on a treatment target may lose precision if the treatment beam must pass through a birefringent layer before reaching the target. In the general case, the birefringent layer splits the treatment beam into ordinary and extraordinary components, which propagate in different directions and form two patterns, displaced from each other, at the target layer. The degree of birefringence and the orientation of the optic axis, which influence the amount of displacement, often vary between workpieces or between loci on the same workpiece. This invention measures the orientation of the optic axis and uses the data to adjust the treatment beam incidence direction, the treatment beam polarization, or both to superpose the ordinary and extraordinary components into a single treatment pattern at the target, preventing the birefringent layer from causing the pattern to be blurred or doubled.

16 Claims, 6 Drawing Sheets

Electronic-photography-based monitoring to measure optic axis effects

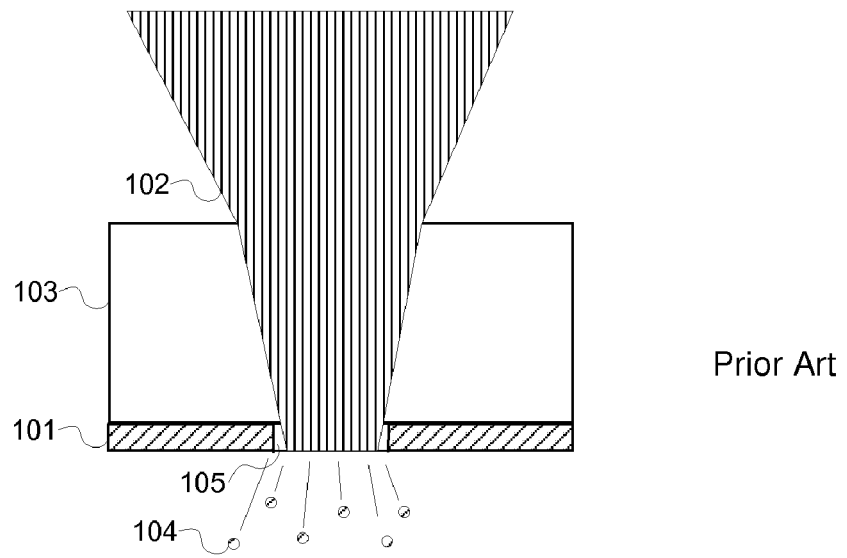
FIG. 1. Bottom-surface laser ablation, an example of optical treatment of a buried target
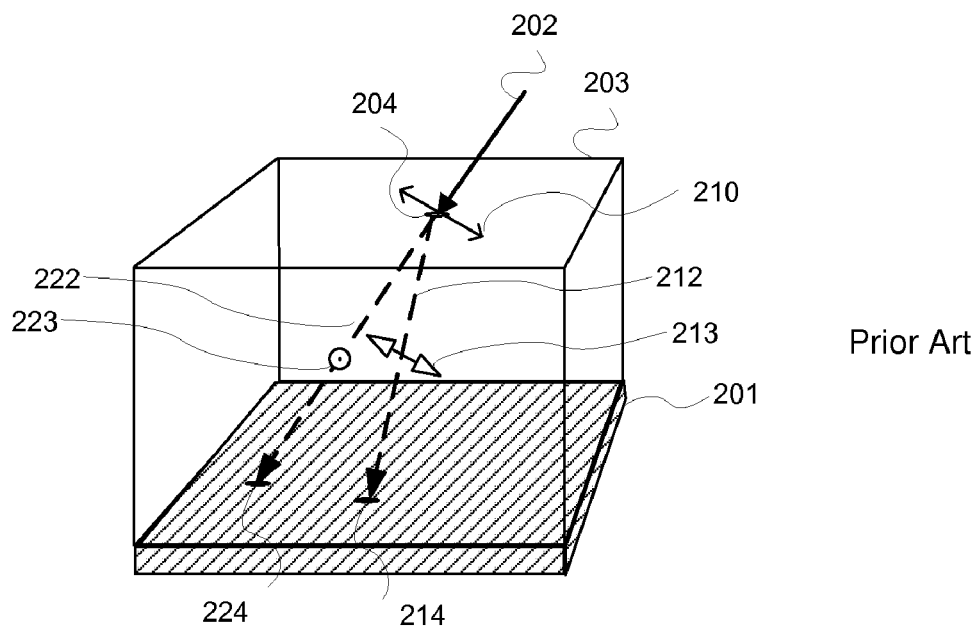
FIG. 2. Birefringent layer splits incoming light into two components refracted at different angles

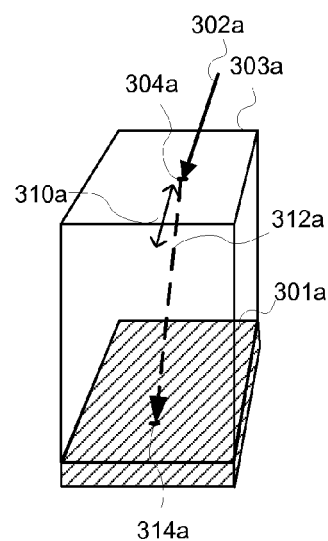
FIG. 3a. Incident beam parallel to optic axis
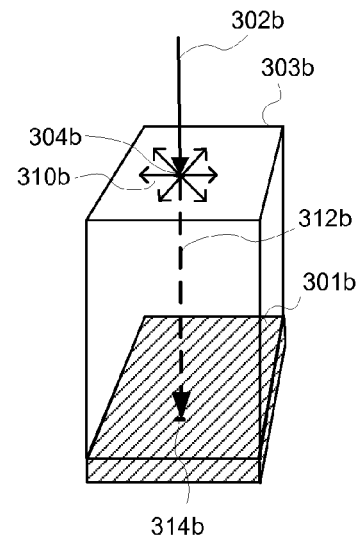
FIG. 3b. Incident beam perpendicular to optic axis and surface of birefringent layer
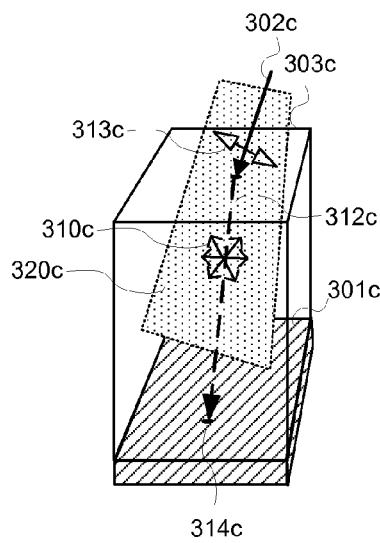
FIG. 3c. Polarization parallel to plane shared by incident beam and optic axis
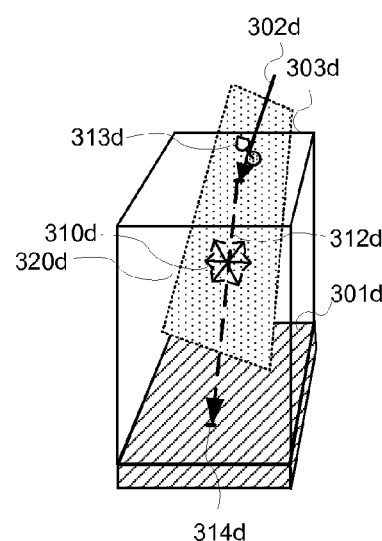
FIG. 3d. Polarization perpendicular to plane shared by incident beam and optic axis

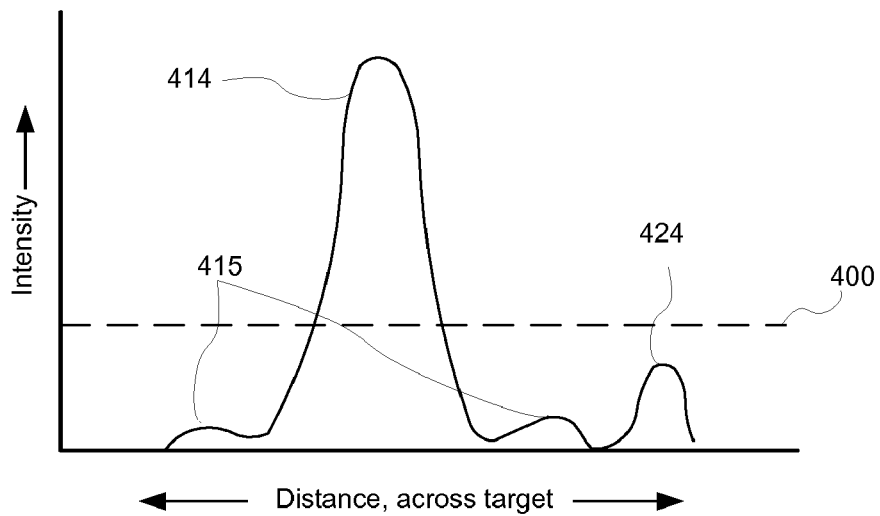
FIG. 4. Effect of treatment threshold or measurement noise level on non-ideal configurations
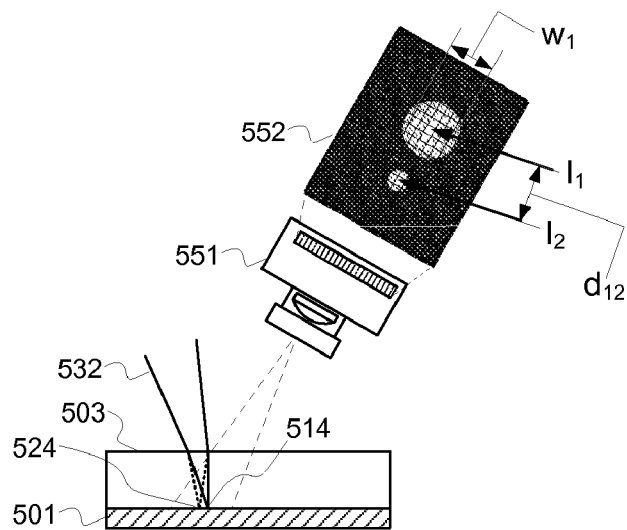
FIG. 5. Electronic-photography-based monitoring to measure optic axis effects

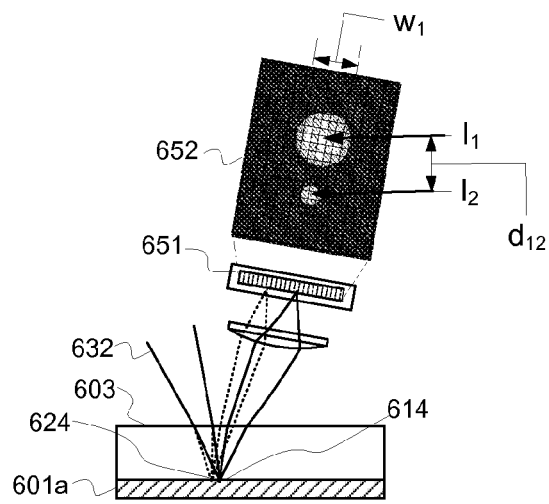
FIG. 6a. Monitoring by mapping reflected light
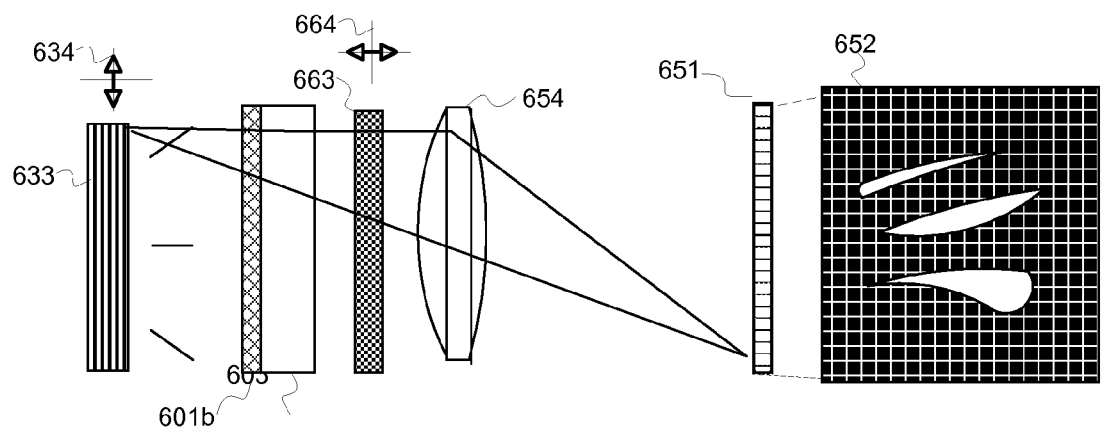
FIG. 6b. Monitoring transmitted light through crossed polarizers

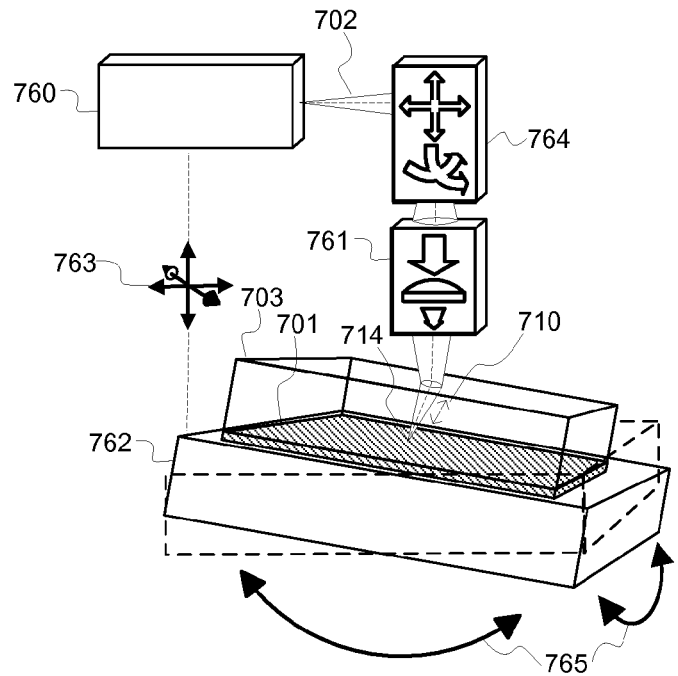
FIG. 7. Example schematic for adjusting treatment or measurement beam to be parallel to optic axis
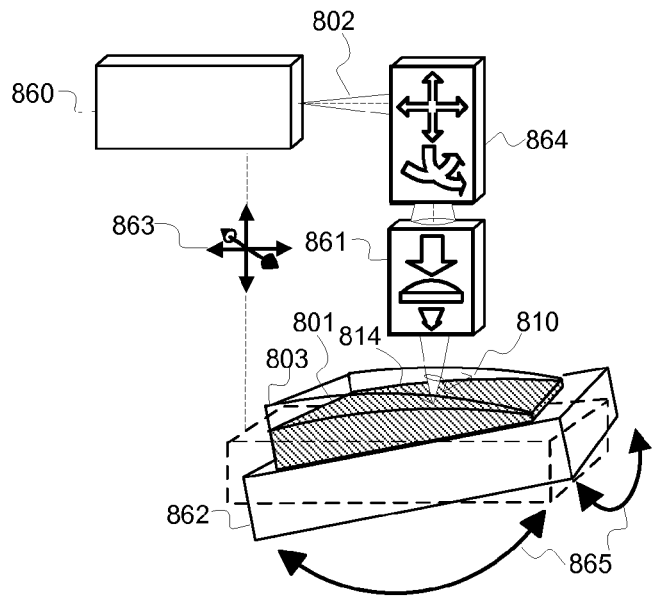
FIG. 8. Example schematic for adjusting treatment or measurement beam to be perpendicular to birefringent-layer entrance surface and optic axis

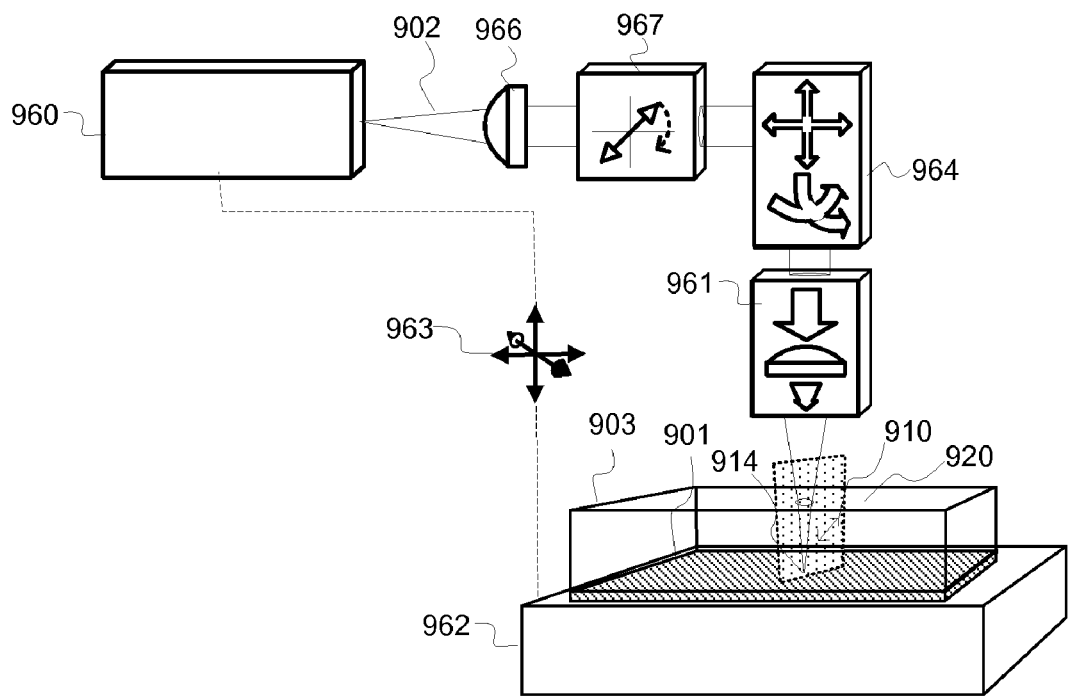
FIG. 9. Example schematic for adjusting treatment or measurement polarization to be perpendicular or parallel to plane of incident beam axis and optic axis

SPATIALLY PRECISE OPTICAL TREATMENT OR MEASUREMENT OF TARGETS THROUGH INTERVENING BIREFRINGENT LAYERS

RELATED APPLICATIONS

None

FEDERALLY SPONSORED RESEARCH AND DEVELOPMENT

None

APPENDICES

None

BACKGROUND OF THE INVENTION

This invention relates generally to optical systems that include control of the polarization of light from an independent light source, and particularly to optical treatment or measurement of a target, where the focus or image of the treatment light must be highly resolved, and where the treatment or measurement light traverses a birefringent material before reaching the target. The optical treatment may be an imaging process, or a process of working the target by means of a laser. The optical measurement may be done with coherent or incoherent light.

Although many optical treatments and measurements are performed on exposed targets, some are performed on targets buried under one or more intervening layers that are substantially transparent to the treatment beam. In this document, a "target" is any location where optical treatment or measurement is desired, whether it lies on an interface surface or within a bulk material. Bottom-surface ablation, as shown in FIG. 1, involves ablating target film 101 by sending treatment beam 102 through superstrate 103 (and sometimes other intervening films). Bottom-surface ablation has the advantage that gravity draws ablated material 104 from ablation cut 105 downward, away from the workpiece, so it does not re-deposit on the workpiece and need to be cleaned off. In addition, if the treatment or measurement beam is Gaussian, the depth of focus (DOF) in the intervening layer is n times the DOF in air, where n is the refractive index of the intervening layer. This makes the focusing or imaging of the beam on the target less sensitive to surface contours and thickness variation of the workpiece.

Other optical treatments that may be performed through intervening layers include, but are not limited to, marking (as described in Herrmann's PCT Application No. WO0061634), annealing and other structural and optochemical changes, pinhole remelting, intentional color-center formation, selective curing, and exposure of wavelength-specific resists, dyes, and other photosensitive material. Measurements may include profilometry, reflectometry, absorption, microscopy, and refractive-index measurements. Reasons for sending the treatment beam through an intervening layer may be that the target is not completely solid and needs to be contained; that the target material needs to be sealed away from ambient atmosphere; or that the treatment must be tamper-proof Measurements are often done through an intervening layer to determine whether the application of the intervening layer altered the characteristics of the underlying layer.

Spatial resolution is critical to some of these optical treatments and measurements. These treatments and measurements include forming a spatially precise pattern of light at the target; for instance, a focused spot, an image, or an interference pattern. However, if the intervening layer is birefringent, the treatment or measurement beam may be split into two polarization components propagating at different speeds and angles. These separate components form separate patterns at the target, so that the resolution of the resulting treatment or measurement is degraded.

FIG. 2 is a simplified illustration of this effect in the general case. Incident beam 202, having arbitrary polarization, enters layer 203 at incident locus 204 (shown here as a point for simplicity; for different beam 202 characteristics, incident locus 204 could be a line or an area). If layer 203 were isotropic, the entire beam would refract along ordinary path 212 and form a pattern 214 on target 201. However, if layer 203 is birefringent, its characteristics include an optic axis 210, shown here with arbitrary orientation. When beam 202 enters layer 203 at incident locus 204, it splits into two orthogonally polarized component beams: ordinary component 212 polarized in direction 213 and extraordinary component 222 polarized in direction 223. The component beams are refracted at different angles because the effective refractive index of layer 203 is different for the ordinary and extraordinary polarizations. Thus the beam forms two spatially separated patterns at the target: pattern 214 from ordinary component 212 and pattern 224 from extraordinary component 222.

Depending on the thickness, the ordinary refractive index, and the birefringent index difference of layer 203 and the incident angle, convergence angle, wavelength, and polarization characteristics of incident treatment beam 202, the superposed patterns 214 and 224 may appear on the target as a single blurred pattern or a doubled pattern, similar to an image viewed through Iceland spar crystal. Even at normal incidence, where the impact of isotropic refractive-index variations on optical treatment and measurement of buried layers is largely mitigated, a birefringent layer can still split the beams along different paths, forming a double pattern at the target, unless the optic axis happens to be parallel or perpendicular to the layer surface. For example, a beam intended to form a 25-micron spot on a target through 3 mm of glass with a birefringent index difference of 0.005 (which is fairly small) was observed to form two overlapping spots with centers separated by 10 microns at the target. Where spot resolution is important to treatment or measurement quality, this is a significant loss of resolution.

A wide range of materials in current industrial use may form a birefringent layer. Many crystalline materials, including liquid crystals, are inherently birefringent. Microcrystalline thin films may also exhibit some localized birefringence. Glasses and polymers, although usually inherently isotropic, can become birefringent from fabrication stresses (especially if fabricated in large-sheet form) or post-fabrication treatments. A prime example is tempered glass.

Tempered glass is preferred for use in glass devices that need to be durable, such as solar panels, outdoor displays, and architectural or vehicle glass. Compared to annealed glass of the same composition, tempered glass is stronger, more thermally resistant, and less hazardous in case of breakage because it breaks into small cuboid fragments rather than irregular shards of varying size. However, the residual strain from the rapid, non-uniform cooling that tempers the glass makes it birefringent. Moreover, the birefringent characteristics are not constant but vary with location on each individual sheet. Transparent polymers are also used for some of the same applications but "optical-grade" polymers that are specially constrained for low birefringence are relatively costly, especially large pieces. With polymers, too, the birefringent characteristics vary within a sheet as well as between individual sheets and from batch to batch.

"Smart" thin-film structures fabricated on glass and transparent polymer are increasingly popular in a wide variety of applications including solar panels, displays and active climate-managing windows and lighting fixtures for buildings and vehicles. Many of these products would also benefit from the safety and durability of tempered glass or the low cost and convenience of non-optical-grade polymer, if precision optical treatment and measurement were possible despite the birefringence. Therefore, a need exists for spatially precise measurement and treatment of a target through an intervening birefringent layer without the pattern-doubling effects that birefringence tends to induce.

BRIEF SUMMARY OF THE INVENTION

An object of this invention is to optically treat or measure buried targets with high spatial precision, despite birefringence in the intervening layers. Accordingly, the invention includes orienting the incident direction of the beam, the polarization of the beam, or both with respect to the material optic axis to match one of the four configurations where the ordinary and extraordinary components are superposed to form a single pattern having substantially the same resolution that it would have in the absence of birefringence.

Another object of this invention is to adapt to changes in the characteristics of the birefringent layer from location to location on the same workpiece and from workpiece to workpiece. Accordingly, the invention includes monitoring the orientation of the optic axis of the birefringent layer at each desired incident locus and formulating the adjustments that will superpose the ordinary and extraordinary components.

Another object of this invention is to make precision optical treatment and measurement through birefringent layers an automatable industrial process. Accordingly, some embodiments of this invention include a control loop that continuously monitors the optic-axis orientation of the birefringent layer and drives alignment devices to superpose the ordinary and extraordinary components based on the monitored data.

BRIEF DESCRIPTION OF THE DRAWINGS

FIG. 1 is a conceptual diagram of bottom-surface ablation, an example of one of several optical treatments that is performed through an intervening transparent layer.

FIG. 2 is a simplified illustration of how an intervening birefringent layer splits an incident treatment beam into ordinary and extraordinary components, which propagate at different angles to form separate patterns at the target.

FIGS. 3a-3d are conceptual diagrams of four configurations of the treatment or measurement beam with respect to the workpiece, each of which results in the ordinary and extraordinary beams being superposed to form a single pattern at the target.

FIG. 4 illustrates the effect of treatment threshold or measurement noise level on the results of non-ideal configurations.

FIG. 5 is a conceptual diagram of monitoring embodiment that monitors the orientation of the optic axis indirectly by monitoring its effect on a focused spot.

FIG. 6a is a conceptual diagram of an alternate monitoring embodiment usable when the surfaces of the target and birefringent layer (and any other intervening layers) are substantially specular and some measurable light from the monitoring beam is reflected from the target surface.

FIG. 6b is a conceptual diagram of an alternate monitoring embodiment that can be used when the target and birefringent layer (and any other intervening layers) transmit at least some measurable light at a wavelength where an image receiver, such as a CCD, is sensitive.

FIG. 7 is an example schematic of a tool adapted to make the treatment or measurement beam parallel to the optic axis.

FIG. 8 is an example schematic of a tool adapted to make the treatment or measurement beam perpendicular to both the workpiece surface and the optic axis in the non-trivial case where the target is not flat and the birefringent layer is not plane-parallel.

FIG. 9 is an example schematic of a tool adapted to adjust the treatment or measurement beam polarization to be parallel or perpendicular to the plane shared by the incident beam and material optic axis.

DETAILED DESCRIPTION OF THE INVENTION

This invention leverages four relative configurations of the optic axis of a birefringent material, the incident direction of a light beam, and the polarization of an incident light beam, which cause all the light to be refracted at the same angle while traveling through the birefringent material. If all the light is refracted at the same angle instead of being split into two components refracted at different angles, the beam can form a single pattern at the target, as if the intervening layer were not birefringent. The four configurations are:

1. The beam propagates through the birefringent layer in a direction parallel to the optic axis. Under this condition, an incident beam of arbitrary polarization will not split into components traveling in different directions.
2. The optic axis is parallel to the entrance surface of the birefringent material at the incident locus, and the beam enters at normal incidence. Under this condition, a beam polarized linearly, parallel or perpendicular to the optic axis, will not split into components at all. A beam of arbitrary polarization will split into two beams traveling at different speeds, but they will travel in the same direction and remain fully overlapped.
3. The beam polarization is linear, oriented parallel to a plane (the "I-OA plane") that contains both the incident beam and the optic axis.
4. The beam polarization is linear, oriented perpendicular to the I-OA plane.

FIGS. 3a-3d are idealized illustrations of configurations 1 through 4, respectively. In FIG. 3a, incident beam 302a may have any polarization entering birefringent layer 303a at incident locus 303c; if incident beam 302a is parallel to optic axis 310a, the refracted beam 312a will form a single pattern on target 301a. In FIG. 3b, incident beam 302b is normal to the entrance surface of birefringent layer 303b, and optic axis 310b is in some orientation parallel to that surface at incident locus 304c. Regardless of its polarization, refracted beam 312b will form a single pattern on target 301b. In FIG. 3c, incident beam 302c is linearly polarized in direction 313c, parallel to the I-OA plane 320c that contains both optic axis 310c (which may have any orientation in that plane) and incident beam 302c. Refracted beam 312c also forms a single pattern on target 301c. In FIG. 3d, incident beam 302d is linearly polarized in direction 313d, perpendicular to the I-OA plane 320c that contains both optic axis 310d (which may have any orientation in that plane) and incident beam 302d. Refracted beam 312d also forms a single pattern on target 301d. The optimal choice among these configurations depends on the nature of the birefringent layer (for instance, its shape, its thickness, and the range of its expected optic-axis orientations) and on the nature of the beam (for instance, its result tolerances, numerical aperture, and working distance).

One skilled in the art would probably not expect an actual pattern-forming beam to behave as well as the idealized rays in FIGS. 3a-3d. For example, if a beam is focused on the target through the birefringent layer to form a converging cone of light, the light enters the birefringent layer at a range of incident angles rather than a single angle. The optic axis, by contrast, tends to have a single orientation, at least over a small area of the workpiece. Therefore, the entire range of beam propagation angles cannot be simultaneously adjusted to an ideal angle with the optic axis. Image-forming beams, like focused beams, also propagate at a range of angles rather than a single angle. Beams forming interference patterns, however, are often collimated so that all the parts of the beam propagate at substantially the same angle. Another obstacle foreseeable by those skilled in the art is the difficulty, and hence the equipment cost, of adjusting the polarization and refracted beam to precisely the correct angle.

Contrary to those logical expectations, however, these configurations have been shown to form very well-resolved patterns with fairly tightly focused beams where the polarization and refraction angles are only substantially near the ideal. This is because of inherent limitations in both treatment and measurement with beams of very low intensity.

FIG. 4 shows the result of slightly non-ideal configuration. An ideal configuration would produce only main peak 414; a non-ideal configuration produces a second peak 424 from the second polarization component, some blurring 415 around main peak 414 from some parts of the beam coming in at non-ideal angles or both. The dotted line 400 represents the low-intensity limit of the process. If the process is an optical treatment, limit 400 may be a threshold, such as an ablation or reaction threshold. If the process is an optical measurement, level 400 could be a noise level of a measurement sensor. Any light reaching the target with intensity below limit 400 will not affect the process. Therefore, even though not all parts of the beam are incident at exactly the ideal angle and the second polarization component 424 is not perfectly extinguished, the treatment or measurement of FIG. 4 will behave as if only the above-the-limit light—that is, main peak 414—were present.

Therefore, if the extinction is "good enough," and if the incident angle range is small (e.g., if the beam is focused or the image is formed at a low numerical aperture) and the birefringent index difference is small or the birefringent layer is fairly thin, experiments show that a pattern of acceptable resolution is formed at the target if the polarization is reasonably linear and properly oriented and the propagation direction is corrected in the center of the beam. Beams that carry most of their intensity in the center, such as the Gaussian beams produced by many lasers, are generally more forgiving of "center-only" propagation-direction correction than beams that have more intensity around the edges.

The low-intensity limit will depend on the wavelength of the beam, its time-dependent intensity characteristics (e.g. pulse profile), and the nature of the target material and any measurement sensor. However, these limits may be available in product specifications or technical publications, or they be measured with reasonable ease; therefore, they can be derived without undue experimentation.

Monitoring the orientation of the optic axis can be important for achieving acceptable results, especially if the optic axis orientation varies from workpiece to workpiece or from one incident locus to another on a single workpiece. A number of approaches to this measurement exist. Because the monitoring method can be independent of the chosen configuration, they will be discussed separately here.

In a preferred embodiment shown in FIG. 5, the orientation of the optic axis is measured indirectly by measuring its effect on a focused spot. Monitor beam 532 should be a wavelength that behaves analogously to the treatment or measurement beam; it may even be a sub-threshold attenuated fraction of the treatment beam or the actual measurement beam. Monitor beam 532 enters through birefringent layer 503 and focuses, if the configuration is not ideally aligned, to two spots 514 and 524 on target 501. Camera 551 forms an image 552 of the two spots on an image receiver, which may be a CCD array or appropriate equivalent. This image is an intensity map, from which such quantities as the relative intensities $I_1$ and $I_2$ of the two spots, their separation $d_{12}$, and the width $w_1$ of the brightest spot at a predetermined cut-off point can be determined. This monitored data can be compared with stored data, such as the maximum allowable ratio $I_2/I_1$, or the maximum allowable width w1 (where, for instance, $d_{12}$ is so small that only one blurry spot appears). The relative tilt between the beam and workpiece, the beam polarization or both can be manipulated until the measured values fall below the stored maxima.

FIG. 6a is a schematic of an alternate monitoring embodiment that can be used when the surfaces of target 601 and birefringent layer 603 (and any other intervening layers) are substantially specular and some measurable light from the monitoring beam is reflected from the target surface. As in FIG. 5, monitoring beam 632 focuses, in the general case, to two spots 614 and 624. However, in this embodiment, imaging lens 653 captures the reflected beams and re-focuses them onto image receiver 651, which may be a CCD array or appropriate equivalent. Received image 652 is analyzed in the same manner as image 552 in FIG. 5, and the workpiece tilt, polarization or both can be manipulated until the image parameters are within a pre-determined acceptable range, corresponding to the desired resolution of the treatment or measurement.

FIG. 6b is a schematic of an alternate monitoring embodiment where the monitoring is done at a wavelength where all the layers of the workpiece transmit at least a measurable amount of light. Extended light source 633 emits light polarized in direction 634. Source 633 may be an incoherent light source masked by a linear polarizer or it may be a light source that "naturally" emits polarized light, such as an active-matrix LCD display. The light from source 633 is transmitted through target layer 601b and birefringent layer 603, then through linear polarizer 663. Linear polarizer 663 is oriented in direction 664 to "cross" the polarization of source 633. Imaging lens 654 images light source 633 onto image receiver 652. If there were no birefringent material between polarized source 611 and crossed polarizer 663, little or no light would be transmitted through crossed polarizer 663, and image receiver 652 would be entirely dark. Birefringence in layer 603, though, changes the polarization of the light so that more light passes through crossed polarizer 663 and reaches image receiver 652. The figure illustrates a birefringent layer with spatially varying birefringence; the light pattern on image receiver 652 is non-uniform. If the birefringence were constant across birefringent layer 603, the illumination would be uniform. Images from the receiver for various can be fed to the measurement or treatment tool as a map of the birefringence characteristics of the workpiece.

Numerous methods also exist in the prior art to monitor the optic axis orientation directly, such as polarization-sensitive optical coherence tomography. In embodiments where the optic axis orientation is monitored directly, the analysis would include the necessary adjustments to relative tilt between the beam and the workpiece, incident polarization angle or both that would produce one of the four desirable configurations.

In some embodiments, the monitoring is done either periodically or continuously during treatment or measurement, with the monitored data providing feedback for a closed control loop that adjusts the configuration whenever the monitored data changes to indicate an out-of-tolerance misalignment. Optionally, some embodiments may include shutters or other devices to extinguish or attenuate the treatment beam, or stop the measurement, if the monitored data approaches the tolerance limit, then cease to extinguish or attenuate the treatment beam or resume measurement when the configuration is readjusted to a comfortable margin. In other embodiments, the monitoring system may "map" the areas of workpiece to be treated or measured and store the data before the treatment or measurement begins. Still other embodiments, for workpieces where the orientation of the optic axis is expected to be uniform over the treatment or measurement, would only require collecting monitored data at a single representative incident locus before treatment or measurement.

Once the alignment parameters to produce a desired configuration are known, the measurement or treatment apparatus can produce the desired configuration in a number of ways.

FIG. 7 is an example schematic of a tool adapted to make the treatment or measurement beam parallel to the optic axis (Configuration 1). Configuration 1 is most advantageous when the optic axis orientation is fairly close to perpendicular to the target surface. Light source 760 produces beam 702. Beam-shaping assembly 761 forms the beam into the desired pattern aimed at target 701. Beam steering assembly 764, which may include optics to fine-adjust the translation and angle of beam 702, may also be present in the beam train. Birefringent layer 703 has optic axis orientation 710 at the locus of incidence. The workpiece (here comprising target layer 701 and birefringent layer 702) is supported by workpiece stage 762. Many treatment and measurement tools include actuators to change the relative position of stage 762 and beam 702 in X, Y, and Z directions 763, either by moving the stage or by moving the light source and its optics. Because light refracted parallel to optic axis 710 will form a single spot 714 regardless of its polarization, only the relative tilt of beam 702 with respect to the workpiece needs to be adjusted. Adjusting this relative tilt by changing the angle of beam 702 using beam steering assembly 764 can be highly precise but the range can be limited by the aperture or aberration sensitivity of beam-shaping assembly 761. By contrast, adjusting this angle by tilting the stage in directions 765 can offer a larger adjustment range but because the stage is generally much more massive than the beam-steering optics; the required actuators will be more expensive and may not be as precise. The choice of either or both of these ways to adjust the tilt will depend on the particulars of the workpiece and process types.

Configuration 2, adjusting the refracted beam to be perpendicular to both the entrance surface of the birefringent layer and its optic axis, is useful in the special case where the optic axis of the birefringent layer is substantially parallel to the entrance surface of the birefringent layer. Where the target is flat and all the layers above it are plane-parallel, the birefringence may not even manifest as a problem in common normal-incidence treatments and measurements. However, when the target layer is not flat or the birefringent layer is not plane-parallel, the birefringence may cause loss of resolution if no adjustment is done.

FIG. 8 is an example schematic of a tool adapted to use Configuration 2 with a workpiece where target 803 is not flat and birefringent layer 803 is not plane-parallel. . Light source 860 produces beam 802. Beam-shaping assembly 861 forms the beam into the desired pattern aimed at target 801. Beam steering assembly 864, which may include optics to fine-adjust the translation and angle of beam 802, may also be present in the beam train. Birefringent layer 803 has optic axis orientation 810 at the locus of incidence. Stage 862 supports the workpiece. Many treatment and measurement tools include actuators to change the relative position of stage 862 and beam 802 in X, Y and Z directions 863, either by moving the stage or by moving the light source and its optics. Because light refracted parallel to optic axis 810 will form a single spot 814 regardless of its polarization, only the relative tilt of beam 802 with respect to the workpiece needs to be adjusted. Here, it needs to be adjusted whenever the angle of the entrance surface of birefringent layer 803 changes enough to unacceptably degrade the resolution of the treatment or measurement. Adjusting this relative tilt by changing the angle of beam 802 using beam steering assembly 864 can be highly precise, but the range can be limited by the aperture or aberration sensitivity of beam-shaping assembly 861. By contrast, adjusting this angle by tilting the stage in directions 865 can offer a larger adjustment range, but because the stage is generally much more massive than the beam-steering optics, the required actuators will be more expensive and may not be as precise. The choice of either or both of these ways to adjust the tilt will depend on the particulars of the workpiece and process types.

Configurations 3 and 4—adjusting the polarization to be parallel or perpendicular, respectively, to the I-OA plane formed by the central axis of the refracted beam and the optic axis of the birefringent layer, are the most useful when the optic axis is neither substantially parallel nor substantially perpendicular to the entrance or target surfaces. However, they impose an extra requirement: that the polarization characteristic of the beam be substantially linear, and that some adjustment can be made to orient the polarization either parallel or perpendicular to the I-OA plane without unacceptable distortion of the pattern from other sources, such as aberrations in the beam-shaping optics.

FIG. 9 is an example schematic of a preferred embodiment of a tool adapted to adjust the treatment or measurement beam polarization to Configuration 3 or 4. Light source 960 produces beam 902. Some light sources, such as some types of laser, produce a beam that is already substantially linearly polarized and collimated. Beam-shaping assembly 961 forms the beam into the desired pattern aimed at target 901. Beam steering assembly 964, which may include optics to fine-adjust the translation and angle of beam 902, may also be present in the beam train. Stage 962 supports the workpiece. Many treatment and measurement tools include actuators to change the relative position of stage 962 and beam 902 in X, Y and Z directions 963, either by moving the stage or by moving the light source and its optics. Birefringent layer 903 has optic axis orientation 910 at the locus of incidence. When beam 902 enters birefringent layer 903, it is refracted. The center of the refracted beam and the local optic axis lie in a plane, the I-OA plane 920. If the polarization of beam 902 is linear and either parallel (Configuration 3) or perpendicular (Configuration 4) to I-OA plane 920, a single effective pattern 914 with optimized resolution will be formed at target 901. Polarization adjuster 967 manipulates the polarization of beam 902 to achieve this.

Most polarization adjustment devices work best with collimated light. Some light sources, such as many lasers, produce light that is already substantially collimated and linearly polarized. For this type of light source, polarization adjuster 967 may be a rotatable half-wave plate, or any other device for rotating the orientation of a linear polarization. If the light source is collimated, but circularly or randomly polarized, polarization adjuster 967 may be a rotatable linear polarizer (although this method can significantly attenuate the beam). If the light source is not collimated, a collimator 966 may be inserted in the beam train before polarization adjuster 967.

The FIG. 9 embodiment is preferred because it does not require disturbing the nominal angle at which the beam reaches the target' too much change in this angle can cause the treatment or measurement pattern to be distorted in some cases. However, if distortion is not a significant risk, alternate embodiments can use a linearly polarized beam of constant orientation and adjust the relative angle between the beam and the entrance surface of the birefringent layer, as in the tools illustrated in FIGS. 6 and 7, until the polarization is either parallel or perpendicular to the I-OA plane.

To summarize, this invention mitigates or eliminates the loss of resolution that can occur when a treatment or measurement beam passes through a birefringent layer before reaching its target. Adjustments to the relative angle of the beam axis and workpiece, or to the beam polarization, or both, produce one of four configurations that minimize the resolution loss from the birefringent layer: (1) beam axis parallel to the optic axis of the birefringent material, (2) beam axis perpendicular to both optic axis and entrance surface of the birefringent layer, (3) polarization parallel to the I-OA plane shared by the beam axis and optic axis, or (4) polarization perpendicular to the I-OA plane shared by the beam axis and optic axis. The adjustments are chosen in response to monitored data about the orientation of the optic axis or about the effects of that orientation on a monitoring beam. Monitored data to determine the optimum adjustment can be collected before or during treatment or measurement. Monitored data can be the input, and adjustment commands the output, of a closed control loop.

Those skilled in the art will recognize that only the claims, not this description or the accompanying drawings, limit the scope of the invention.

The inventor claims:

1. An apparatus for optically treating or measuring a target through a birefringent layer having an optic axis, comprising:
   a light source adapted to generate a treatment or measurement beam having an incidence direction and a polarization characteristic, and a monitor beam;
   a monitoring apparatus for monitoring an orientation of the optic axis or effects that indicate the orientation; and
   an alignment apparatus for adjusting the relative orientation of the optic axis and at least one of the incidence direction or the polarization characteristic based on the monitored data;
   where
   the monitor beam forms at least a first spot and a second spot on the target with respective intensities $I_1$ and $I_2$, widths $W_1$ and $W_2$, and a distance d between centers of the two spots, where $I_1$ is greater than $I_2$, and $W_1$ is greater than $W_2$;
   the monitor beam enters the birefringent layer at an incident locus;
   the birefringent layer can split beams with some combinations of incidence direction and polarization characteristic into ordinary and extraordinary components propagating at different angles; and
   an optimal adjustment of the alignment apparatus, based on at least one of $I_1$ and $I_2$, $W_1$ or d, creates an acceptably resolved pattern at the target.

2. The apparatus of claim 1, wherein the optimal adjustment, based on at least one of $I_1$ and $I_2$, $W_1$ or d, causes the beam to be refracted substantially parallel to the optic axis of the birefringent layer at the incident locus.

3. The apparatus of claim 1, wherein the optimal adjustment, based on at least one of $I_1$ and $I_2$, $W_1$ or d, causes the beam to be refracted substantially perpendicular to the optic axis of the birefringent layer at the incident locus.

4. The apparatus of claim 1, wherein
   the polarization characteristic is substantially linear at a polarization angle; and
   the optimal adjustment, based on at least one of $I_1$ and $I_2$, $W_1$ or d, causes the beam to be refracted substantially in the same plane as the dominant polarization direction and the optic axis at the incident locus.

5. The apparatus of claim 1, wherein
   the polarization characteristic is substantially linear at a polarization angle; and
   the optimal adjustment, based on at least one of $I_1$ and $I_2$, $W_1$ or d, causes the polarization angle to be substantially parallel to the plane of the incident beam and the optic axis at the incident locus.

6. The apparatus of claim 1, wherein
   the polarization characteristic is substantially linear at a polarization angle; and
   the optimal adjustment, based on at least one of $I_1$ and $I_2$, $W_1$ or d, causes the polarization angle to be substantially perpendicular to the plane of the incident beam and the optic axis at the incident locus.

7. The apparatus of claim 1, further comprising a storage medium configured to store reference data, for use for said optional adjustment of the alignment apparatus, based on at least one of $I_1$ and $I_2$, $W_1$ or d.

8. The apparatus of claim 7, wherein the monitoring apparatus is configured to collect monitored data for an entire area of a workpiece to be measured or treated.

9. The apparatus of claim 1, wherein the monitoring apparatus is configured to collect monitored data from a workpiece during treatment or measurement.

10. The apparatus of claim 9, further comprising a controller coupled to the monitoring apparatus and alignment apparatus, and adapted to perform functions comprising:
    collecting data from the monitoring apparatus;
    calculating the optimal adjustment of the alignment apparatus, based on at least one of $I_1$ and $I_2$, $W_1$ or d, to enable the treatment or measurement beam to project into a focused spot, an image or an interference pattern of predetermined characteristics on the target; and
    commanding the alignment apparatus to make the optimal adjustment.

11. The apparatus of claim 10, wherein the controller is adapted to perform further functions comprising:
    attenuating or extinguishing the treatment or measurement beam in response to monitored data; and
    ceasing to attenuate or extinguish the treatment or measurement beam in response to monitored data.

12. The apparatus of claim 1, wherein the monitoring apparatus is configured to monitor the orientation of the optic axis indirectly by monitoring the polarization of light reflected, diffracted, or scattered through the birefringent layer.

13. The apparatus of claim 1, wherein the monitoring apparatus is configured to form an image of the two spots to provide $I_1$ and $I_2$, $W_1$ or d for making the optimal adjustment.

14. The apparatus of claim 13, wherein the monitoring apparatus comprises a camera.

15. The apparatus of claim 14, wherein the extended polarized light source is an LCD screen.

16. The apparatus of claim 14, wherein the camera comprises a CCD array.

* * * * *